US010610632B2

(12) United States Patent
Golarits et al.

(10) Patent No.: US 10,610,632 B2
(45) Date of Patent: Apr. 7, 2020

(54) METHOD AND CONTROL APPARATUS FOR DETERMINING AND ADJUSTING A FLOW RATE OF A BLOOD DELIVERY PUMP

(71) Applicant: B. BRAUN AVITUM AG, Melsungen (DE)

(72) Inventors: István Golarits, Budapest (HU); Botond Tényi, Budakalász (HU)

(73) Assignee: B. Braun Avitum AG, Melsungen (DE)

( * ) Notice: Subject to any disclaimer, the term of this patent is extended or adjusted under 35 U.S.C. 154(b) by 561 days.

(21) Appl. No.: 14/940,505

(22) Filed: Nov. 13, 2015

(65) Prior Publication Data

US 2016/0166755 A1    Jun. 16, 2016

(30) Foreign Application Priority Data

Dec. 10, 2014 (EP) ..................................... 14197218

(51) Int. Cl.
*A61M 1/36* (2006.01)
*F04B 43/00* (2006.01)
(Continued)

(52) U.S. Cl.
CPC ........ *A61M 1/3644* (2014.02); *A61M 1/3621* (2013.01); *A61M 1/3624* (2013.01);
(Continued)

(58) Field of Classification Search
CPC .............. A61M 1/1006; A61M 1/1039; A61M 1/1086; A61M 1/3621; A61M 1/3624;
(Continued)

(56) References Cited

U.S. PATENT DOCUMENTS

| 4,108,575 A | 8/1978 | Schäl |
| 4,432,230 A | 2/1984 | Stahler et al. |

(Continued)

FOREIGN PATENT DOCUMENTS

| CN | 1321095 A | 11/2001 |
| CN | 101466419 A | 6/2009 |

(Continued)

OTHER PUBLICATIONS

European Search Report for EP 14197218.2 dated Jun. 23, 2015.
(Continued)

*Primary Examiner* — Benjamin J Klein
(74) *Attorney, Agent, or Firm* — RatnerPrestia

(57) ABSTRACT

Flow rate of a blood delivery pump of a blood treatment apparatus is determined and adjusted by connecting a fluid filled container with an extracorporeal blood line of the blood treatment apparatus, performing a priming step to prime the extracorporeal blood line by driving the blood delivery pump at a predetermined theoretical delivery rate to deliver fluid from the filled container into the extracorporeal blood line, determining the loss of fluid of the fluid filled container due to delivery of fluid into the extracorporeal blood line during priming, and determining a correction factor by comparison of a value for an amount of fluid delivered under the theoretical delivery rate with a value for the amount of fluid actually delivered.

18 Claims, 2 Drawing Sheets

(51) Int. Cl.
*F04B 49/06* (2006.01)
*F04B 43/12* (2006.01)
*F04B 23/02* (2006.01)
*F04B 49/00* (2006.01)
*A61M 1/10* (2006.01)

(52) U.S. Cl.
CPC ........ *A61M 1/3643* (2013.01); *A61M 1/3652* (2014.02); *A61M 1/3663* (2013.01); *F04B 23/02* (2013.01); *F04B 43/0081* (2013.01); *F04B 43/12* (2013.01); *F04B 43/1253* (2013.01); *F04B 49/00* (2013.01); *F04B 49/065* (2013.01); *A61M 1/1006* (2014.02); *A61M 1/1039* (2014.02); *A61M 1/1086* (2013.01); *A61M 2205/3334* (2013.01); *A61M 2205/3393* (2013.01)

(58) Field of Classification Search
CPC .............. A61M 1/3643; A61M 1/3644; A61M 1/3652; A61M 1/3663; A61M 2202/3334; A61M 2202/3393
See application file for complete search history.

(56) References Cited

U.S. PATENT DOCUMENTS

| | | |
|---|---|---|
| 4,468,219 A | 8/1984 | George et al. |
| 4,596,550 A | 6/1986 | Troutner |
| 4,769,001 A | 9/1988 | Prince |
| 5,112,298 A | 5/1992 | Prince et al. |
| 5,200,090 A | 4/1993 | Ford et al. |
| 5,578,223 A | 11/1996 | Bene et al. |
| 5,776,345 A | 7/1998 | Truitt et al. |
| 5,910,252 A | 6/1999 | Truitt et al. |
| 5,947,692 A | 9/1999 | Sahlin et al. |
| 6,325,775 B1 | 12/2001 | Thom et al. |
| 6,348,156 B1 | 2/2002 | Vishnoi et al. |
| 6,691,047 B1 | 2/2004 | Fredericks |
| 8,140,274 B2 | 3/2012 | Gagel et al. |
| 9,089,639 B2 | 7/2015 | Breuel et al. |
| 2009/0211962 A1* | 8/2009 | Min ................ A61M 1/3693 210/378 |
| 2010/0168925 A1 | 7/2010 | Hilgers et al. |
| 2012/0193290 A1* | 8/2012 | Breuel ................ A61M 1/16 210/646 |
| 2015/0292529 A1 | 10/2015 | Thiebaud et al. |

FOREIGN PATENT DOCUMENTS

| | | |
|---|---|---|
| CN | 103379926 A | 10/2013 |
| DE | 2535650 A1 | 2/1977 |
| DE | 69229746 T2 | 1/2000 |
| DE | 10112848 B4 | 9/2008 |
| DE | 10 2011 010067 | 8/2012 |
| EP | 0513421 A1 | 11/1992 |
| EP | 0522075 B1 | 1/1993 |
| EP | 0578338 A2 | 1/1994 |
| EP | 0723463 B1 | 3/2001 |
| EP | 2749858 B1 | 4/2018 |
| JP | 01503198 A | 11/1989 |
| JP | 05508560 A | 12/1993 |
| JP | 06315530 A | 11/1994 |
| JP | 2003508179 A | 3/2003 |
| JP | 2014513990 A | 6/2014 |
| WO | 8806466 A1 | 9/1988 |
| WO | 9923386 A1 | 5/1999 |
| WO | WO 01/17652 | 3/2001 |
| WO | 0178808 A1 | 10/2001 |
| WO | 03055542 A1 | 7/2003 |
| WO | 2004069308 A1 | 8/2004 |
| WO | 2006097199 A1 | 9/2006 |
| WO | 2006123197 A1 | 11/2006 |
| WO | 2014068475 A2 | 5/2014 |

OTHER PUBLICATIONS

Japanese Notification of Reason for Rejection for Japanese Application No. 2015-191793, with English translation, dated Oct. 23, 2018—4 pages.
Chinese Office Action for Chinese Application No. 201510750491.6, dated Feb. 28, 2019, with translation, 20 pages.
Klespitz et al., "Peristaltic Pumps—A Review on Working and Control Possibilities", IEEE 12th International Symposium on Applied Machine Intelligence and Informatics, 2014, pp. 191-194.
Klespitz et al., "Identification and Control of Peristaltic Pumps in Hemodialysis Machines", IEEE 14th International Symposium on Computational Intelligence and Informatics, 2013, pp. 83-87.
Hörl et al., "Replacement of Renal Function by Dialysis", Drukker; Pasons and Maher, 5th Edition, 2004, 12 pages.
European Opposition for European Patent No. EP3031485, dated Aug. 20, 2019 with translation, 54 pages.

\* cited by examiner

METHOD AND CONTROL APPARATUS FOR DETERMINING AND ADJUSTING A FLOW RATE OF A BLOOD DELIVERY PUMP

CROSS REFERENCE TO RELATED APPLICATIONS

This application claims priority to European application EP 14197218.2 filed Dec. 10, 2014, the contents of such application being incorporated by reference herein.

FIELD OF THE INVENTION

The invention relates to a method and a control apparatus for determining and adjusting a flow rate of a blood delivery pump of a blood treatment apparatus.

In renal replacement therapies the patient's extracorporeal blood delivery flow provides an essential parameter indicative for performance. Usually, a flow rate lower than a set value is considered to be disadvantageous for treatment. The patient's blood is usually delivered by a peristaltic pump using plastic disposable pump segment tubes. It is a problem, that there may occur an error in measurement of this blood flow, for example due to deviation caused by plastic disposable tubing production related parameters like e.g. production accuracy of internal diameter, wall thickness, hardness and/or material composition. These parameters may differ from batch to batch of a production series. In order to achieve more accurate delivery it is important to eliminate or to at least reduce the influence of such production batch related errors to a metered flow rate.

DESCRIPTION OF THE RELATED ART

U.S. Pat. No. 4,432,230 discloses a method of determining the flow rate of a pump under test comprising the steps of (a) pumping fluid into a receptacle for a selected period of time via an orifice having a known maximum flow rate, said fluid being under sufficient pressure to maintain the said maximum flow rate through said orifice so that the volume of fluid pumped into the receptacle during said selected time period is known; (b) evacuating the receptacle using the pump under test; (c) measuring the time period required to perform step (b); (d) calculating the flow rate of the pump under test from the known volume of fluid evacuated and the time period required to perform step (b). The patent further discloses an apparatus for determining the flow rate of a pump under test comprising a fluid receptacle, an orifice having a known maximum flow rate, means for pumping fluid via said orifice into said receptacle under sufficient pressure to maintain the maximum flow rate through said orifice, means for alternately connecting one of said pumping means and said pump under test to said receptacle whereby the receptacle is filled by said pumping means and evacuated by the pump under test, control means for operating said pumping means for a selected time period whereby the volume of fluid in the receptacle is known and for measuring the time required for the pump under test to evacuate the receptacle and calculating the flow rate of the pump under test from the known volume of fluid evacuated from the receptacle and the time required to evacuate it.

U.S. Pat. No. 5,112,298 discloses a simplified fluid separation method and device for various apheresis procedures including plasmapheresis. An apheresis method comprises the steps of (a) fluidly connecting a blood separation device to the vasculature of a human subject, (b) operating at least one pump to withdraw whole blood from the human subject and to move said whole blood into said separation device; (c) providing a single weighing device having a first blood fraction container and a second blood fraction container positioned thereon, such that said weighing device will measure the combined weight of the said first blood fraction container and said second blood fraction container, along with any material contained therein; (d) recording an initial weight on said weighing device when said first blood fraction container and said second blood fraction container are empty; (e) operating said separation device to fraction the whole blood into at least a first blood fraction and a second blood fraction; (f) recording a second weight on said weighing device after said first blood fraction and said second blood fraction have been collected in said first blood fraction container and said second blood fraction container; (g) providing a fluid connection between said first blood fraction container and said human subject; (h) operating at least one pump to reinfuse said first blood fraction, through said fluid connection, into said human subject; and (i) recording a third weight on said weighing device after said first blood fraction has been removed from said first blood fraction container reinfused into said human subject.

U.S. Pat. No. 5,947,692 discloses a controller for a peristaltic pump suited for processing blood and biological cellular suspensions and including a rotor assembly and a pump tube arranged to be engaged by the rotor assembly and having an inlet, the controller comprising a sensing element for sensing pressure at the inlet and providing a sensed output Pi, and a command module having an input coupled to the sensor to receive Pi, the command module including a processing element that derives a scale factor SPi that varies according to a step function of Pi and equals a first nonvariable value when Pi lays in a first defined zone of inlet pressures, and equals a second nonvariable value, different than the first nonvariable value, when Pi lays in a second defined zone of inlet pressures different than the first defined zone of inlet pressures, the command module also including an output that generates a pump speed command S based, at least in part, upon SPi.

U.S. Pat. No. 8,140,274 discloses a method for determining and adjusting the effective delivery rate of a peristaltic pump, with which liquid is delivered in an elastic hose pipe, comprising determining the pressure in the hose pipe upstream of the pump and the nominal speed of the pump, calculating the effective delivery rate on the basis of the nominal speed of the pump and the pressure in the hose pipe upstream of the pump, wherein the calculation of the effective delivery rate takes place on the basis of the nominal speed of the pump and the pressure in the hose pipe upstream of the pump in dependence on the running time of the pump, the calculating including multiplying the stroke volume of the pump by the nominal speed of the pump and correcting the product of the stroke volume and the nominal speed of the pump by a correction function describing the dependence of the stroke volume of the pump on its running time and the pressure in the hose pipe upstream of the pump in order to determine the effective delivery rate, determining a correction factor for the nominal pump speed that corresponds to a change of the effective delivery rate from the calculated delivery rate to a predetermined desired delivery rate and changing the effective delivery rate to the desired delivery rate by adjusting the nominal pump speed to an adjusted speed determined by multiplying the determined nominal speed by the correction factor.

U.S. Pat. No. 7,112,273 discloses a device for balancing the flow of fluids in a blood treatment system, the device comprising a balancing mechanism having inlets and outlets for a first flow of fluid that includes renal waste and a second flow of fluid including fluid to be infused into a patient, at least one pressure sensor configured to measure a pressure difference between at least one of said inlets relative to a respective outlet, the balancing mechanism employing a volumetric system that is subject to variation in relative flow volume rates due to variations in differences between respective inlet and outlet pressures of said first and second flows, said balancing mechanism configured to receive a compensation signal and adjust a balance between a ratio of said first flow to said second flow responsively to said compensation signal to maintain a correct fluid balance of the patient, a controller configured to generate said compensation signal responsively to at least one pressure measurement by said at least one pressure sensor, said at least one pressure measurement including at least one of said differences between respective inlet and outlet pressures of said first and second flows.

BACKGROUND OF THE INVENTION

It is further known that the production batch related error of a disposable blood pump segment tube can be reduced by "calibrating" the pump delivery with every tube segment before use. However, this requires an accurate measurement system. Usually, in acute renal replacement therapy apparatus the patient balance is controlled by using a weight measurement system. This system is also used for automatic priming and testing the substitution/dialysis fluid circuit in preparation, but is not applied for the blood delivery system. For priming the blood side tubing usually a filled saline bag is applied to the IV pole connected to the arterial line of the blood line. A waste bag is connected to the venous line and is placed on a load cell to determine the weight of the fluid contained in the waste bag and to perform the "calibration" of the real peristaltic blood pump delivery. It is a disadvantage that a very slow automatic calibration and priming operation is the result and that it may require manual intervention, since the calibration can only be started after the disposable system is primed, i.e. when the fluid reaches the waste bag. Such a calibration procedure therefore requires extra priming time. Additionally, the accuracy of measurement is not satisfying. This is because during priming the system (especially when priming a hemofilter containing small capillary) air removal from the piping is slow. Further, even during the calibration phase air bubbles are replaced by a certain flow of fluid, which certain flow of fluid cannot be determined by the load cell.

Another large effect and disadvantage on the accuracy of the blood flow is the influence of the pump inlet pressure to the behaviour of the piping. A negative pressure may result in some collapsing of the pump segment tube thus making it oval. Such a deformation of the pump segment tube may reduce the cross section area of the latter, which results in a decrease of the delivery volume. To the contrary, positive inlet pressure may result in enlargement of the cross section area, which results in an increase of the delivery volume. Since a flow lower than a desired flow is considered as negative for treatment and the blood pump inlet pressure ("arterial" pressure) usually is negative because of a thin patient connection provided e.g. by a catheter or a needle, especially errors due to a negative inlet pressure should be reduced. This is especially true in acute renal replacement therapies where usually a catheter is connected into a patient's vein.

It is a disadvantage of the current state of the art solutions, that any error of an extracorporeal blood delivery flow due to deviations of the pumping system caused for example by deviations of different production batches usually cannot be compensated before therapy or at least with a time consuming and inaccurate method.

SUMMARY OF THE INVENTION

It is an object of the invention to provide a method for calibrating a pump of a apparatus for extracorporeal blood treatment, the pump providing a flow of a patient's blood in the apparatus, which method is simple, not time consuming and provides a reliable calibration of the pump, such that the patient's extracorporeal blood delivery flow can be provided, maintained and controlled with high accuracy.

To achieve this aim, according to aspects of the invention there is provided a method for determining and adjusting a flow rate of a blood delivery pump of a blood treatment apparatus, the method comprising:

connecting a container filled with fluid, also designated as supply container, preferably a bag, with an extracorporeal blood line of the blood treatment apparatus, performing a priming step to prime the extracorporeal blood line by driving the blood delivery pump at a predetermined theoretical delivery rate to deliver fluid from the filled container into the extracorporeal blood line, determining the loss of fluid of the container due to delivery of fluid into the extracorporeal blood line during priming, determining a correction factor by comparison of an amount of fluid delivered under the theoretical delivery rate with an amount of fluid delivered in real.

The extracorporeal blood line may in particularly be a pipe, a conduit, a fluid system or the like. Preferably, the extracorporeal blood line may be a disposable plastic tubing for single use. It is a significant advantage of the invention that a very accurate determination of the flow rate and therefore adjustment of the flow rate it ensured. The reason for this is, that the determination of the amount of fluid delivered by the blood pump during priming takes place before the fluid enters the blood lines and passes the hemofilter of the extracorporeal blood line. Therefore, determination of the flow rate is not influenced by air bubble removal usually taking place during priming.

It is within the present invention, that an error occurring in extracorporeal blood flow can be reduced by "calibrating" the blood pump and determining a correction factor, which may be a constant for the blood pump or a constant for any segment or pump stroke of the blood pump (a so called segment delivery constant). In one embodiment, the correction factor may be determined by measurement of the amount of fluid withdrawn from the fluid filled container during an automatic priming procedure, when a new extracorporeal blood line is applied to the blood treatment apparatus, usually before start of therapy or within a change of the extracorporeal blood line. According to aspects of the invention, first an accurate calibration is performed from the container, which contains the priming fluid. In one embodiment the container hangs on or is arranged on a load cell and is connected to the arterial inlet of the blood pump. The blood pump runs with a given estimated delivery rate, or with other words with a given estimated speed, e.g. inlet rotational speed, for a given amount time, which may be the complete priming process or a part thereof. The estimated transferred amount of fluid, e.g. the estimated volume and/or weight of transferred fluid, is compared to the amount of fluid withdrawn from the container, e.g. is compared with the change of weight and/or volume of the container determining the real amount transferred.

According to one embodiment of the invention, the fluid filled container may be connected to an arterial line or arterial port of the extracorporeal blood line. Additionally, a waste container can be connected with the extracorporeal blood line, preferably to an outlet of the extracorporeal blood line, in particular to a venous line or a venous port of the extracorporeal blood line. At least one of the container and the waste container may be a bag. The priming fluid, which is contained in the fluid filled container, may in particular be saline.

According to one embodiment of the invention, the loss or outflow of fluid during the priming step or during a certain time period of the priming procedure may be determined by measuring the weight of the fluid filled container, in particular by calculating the weight of the amount of fluid delivered out of the fluid filled container into the extracorporeal blood line during priming. In one embodiment, the weight of the container is measured at the beginning and at the end of the priming process or the calibration and based on these two values the correction facture can be determined. In another embodiment, the weight of the container may be supervised continuously or at least iteratively, such that a row of weight values are recorded and may be used to calculate the correction factor or several correction factors. Alternatively to the weight, other parameters may be used to determine the amount of fluid withdrawn from the container, for example the volume or the change of volume of the container, which may be the case if a flexible container, e.g. a bag, is used.

According to one embodiment of the invention, the pump may be a peristaltic pump comprising an elastic deformable fluid conduit, in particular a tube, a stator or supporting surface supporting said fluid conduit and a rotor. Said rotor comprises at least two squeezing elements, for example in form of rollers, which during rotation of the rotor deform the fluid conduit. The peristaltic pump therefore at least provides two pumping strokes or pumping segments, each stroke or segment being provided by the volume of the fluid conduit squeezed between adjacent squeezing elements, which is the delivery volume per stroke/segment. In case the blood pump having two or more pumping segments or strokes, according to one embodiment of the invention, an individual segment correction factor (stroke correction factor) may be determined for each pumping segment/stroke. In this case the correction factor for the blood pump, which also may be called calibrated pump segment/stroke delivery constant value, can be increased with a given extent to keep the flow change within the acceptable tolerance range in the usual arterial pressure range. With other words, the correction factor or the individual segment/stroke correction factor may be increased to keep deviations of flow delivered by the blood pump within a tolerance range in a usual inlet arterial flow range.

According to one embodiment of the invention, the predetermined theoretical delivery rate is constant, at least during the step of priming, in which case it is easy to calculate the correction factor for the blood pump.

It is within the scope of invention to combine the aforementioned embodiments in any possible manner.

One can also say that according to aspects of the invention an extracorporeal blood flow error is reduced by "calibrating" the pump segment delivery constant with weight measurement during automatic priming at applying a new disposable blood line (before therapy start or blood line change). A filled saline bag may be hung on one of the load cells (e.g. "effluent" one) of the apparatus, which usually are used to control the blood exchange of the patient, by connecting it to the "arterial" line (just the opposite as the usual priming setup) and placing a waste bag on the IV pole by connecting it to the "venous" line. For automatic priming a new disposable extracorporeal blood circuit (before therapy start or blood line change), the blood pump delivers the fluid from this saline bag to the waste bag on the IV pole. So the "calibration" of the peristaltic blood pump tubing segment can be performed as part of the priming process resulting in a quicker calibration and overall priming process. Additionally, a very accurate calibration is ensured, since weight measurement happens before the blood lines and hemofilter not influenced by the air bubble removal.

By the invention the negative inlet related blood flow error can be reduced by changing the above calibrated pump segment constant by "pre-tensioning" the pump or the driving of the pump to deliver higher volume. It is done by decreasing the pump segment constant value with a given extent, which increases the pump rotation to keep the blood flow within the acceptable tolerance range in the usual inlet "arterial" pressure range. By the invention the initial production batch related error of the blood pump segment tube can be eliminated quickly and accurately.

Another aspect of the invention relates to a control apparatus for determining and adjusting a flow rate of a blood delivery pump of a blood treatment apparatus, wherein said blood treatment apparatus comprises a container, which is filled with fluid and which is connected with an extracorporeal blood line of the blood treatment apparatus; the blood delivery pump for delivering fluid from the container into an extracorporeal blood line; and determining means for determining the loss of fluid from the container due to delivery of fluid into the extracorporeal blood line. The control apparatus controls the blood delivery pump such that the fluid is delivered from the container into the extracorporeal blood line at a predetermined theoretical delivery rate, and determines a correction factor by comparing an amount of fluid delivered under the theoretical delivery rate with the loss of fluid determined by the determining means.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
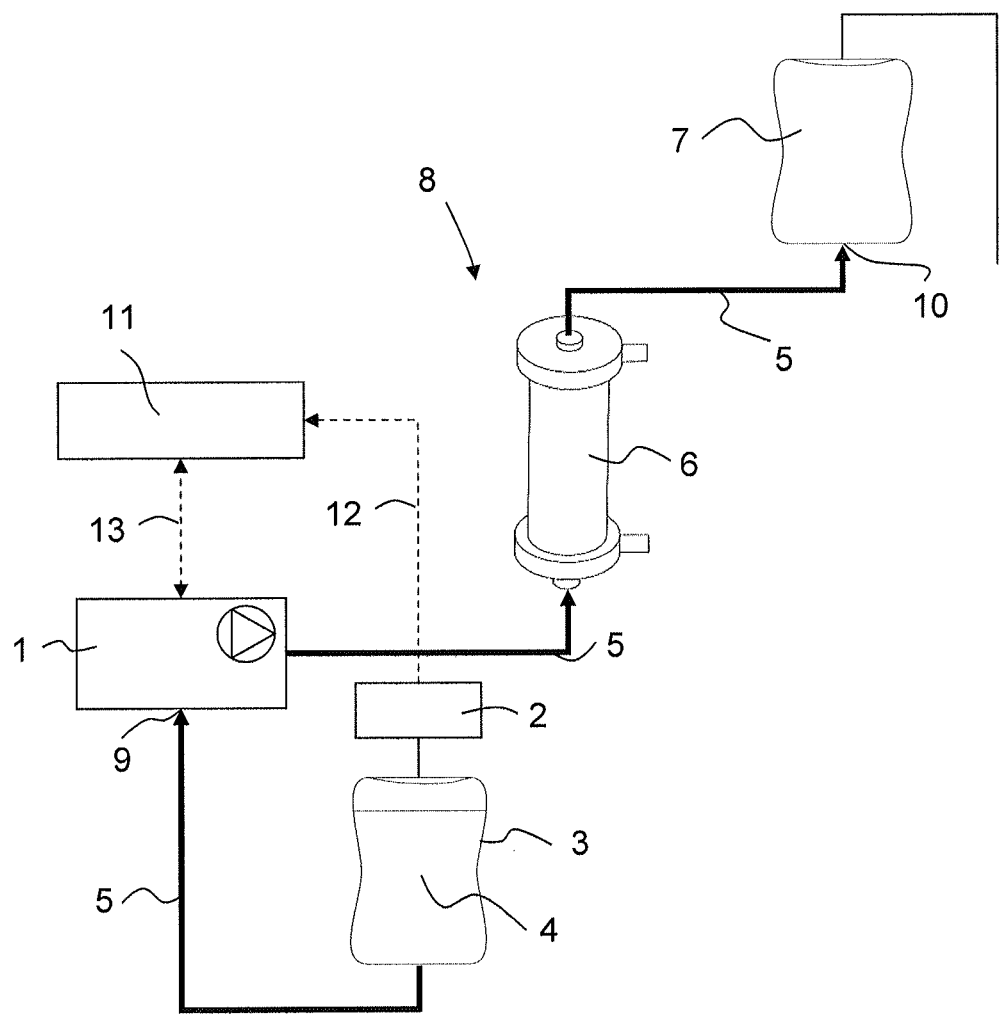
FIG. 1 shows a schematic overview of a blood treatment apparatus including a control apparatus according to aspects of the invention.

The FIG. 1 shows part of a blood treatment apparatus suitable for performing the method of the invention. The apparatus comprises a peristaltic pump 1, a load cell 2, a container 3 in form of a bag 3 filled with a fluid 4, e.g. saline, used for priming, a disposable tubing set 5 with a hemofilter 6 or dialyzer 6 and a waste container 7 in form of an empty bag 7 for receiving the priming fluid pumped through the tubing set 5. The tubing set 5 provides an extracorporeal blood line 8 of the blood treatment apparatus.

The supply container 3 filled with priming fluid 4 is placed on the load cell 2 or hangs on the load cell 2. The supply container 3 is further connected to an inlet 9 of the peristaltic pump 1. The waste container 7 for receiving priming collection pumped through the extracorporeal blood line 8 is connected to an outlet 10 of the disposable tubing set 5.

For priming the disposable tubing set 5 with hemofilter 6 the peristaltic pump 1 delivers the fluid 4 from the supply container 3 through the tubing set 5 and the extracorporeal blood line 8 to the waste container 7. To perform calibration or determination of the flow rate of the pump 1, the latter is started or driven with a given pump rotation for a given time.

To determine the flow rate of the pump 1, the difference of weight resting on the load cell 2, i.e. the weight of the supply container 3 and the fluid 4 contained therein, at the beginning as well as at the end of the calibration or the priming procedure or part thereof, is measured and fed to a controller 11, as indicated with arrow 12. According to one embodiment of the invention, the weight acting on the load cell 2 is constantly measured. By using the aforementioned values of weight or data concerning change of weight, the amount of fluid 4 delivered by the pump 1 can be calculated. Additionally, from this amount delivered and the calibration time the actual so called "pump segment constant" can be calculated. By applying this pump segment constant for the blood pump the production batch related error of the pump segment tube can be eliminated by feeding a corrected drive signal 13 from the controller 11 to the pump 1.

Negative inlet related blood flow error can be reduced by changing the above calibrated pump segment constant by "pre-tensioning" the pump 1 to deliver higher volume/amount of fluid 4. It is done by decreasing the pump segment constant value by a given extent, which increases the pump rotation to keep the blood flow within the acceptable tolerance range in the usual inlet "arterial" pressure range.

Figure 2:
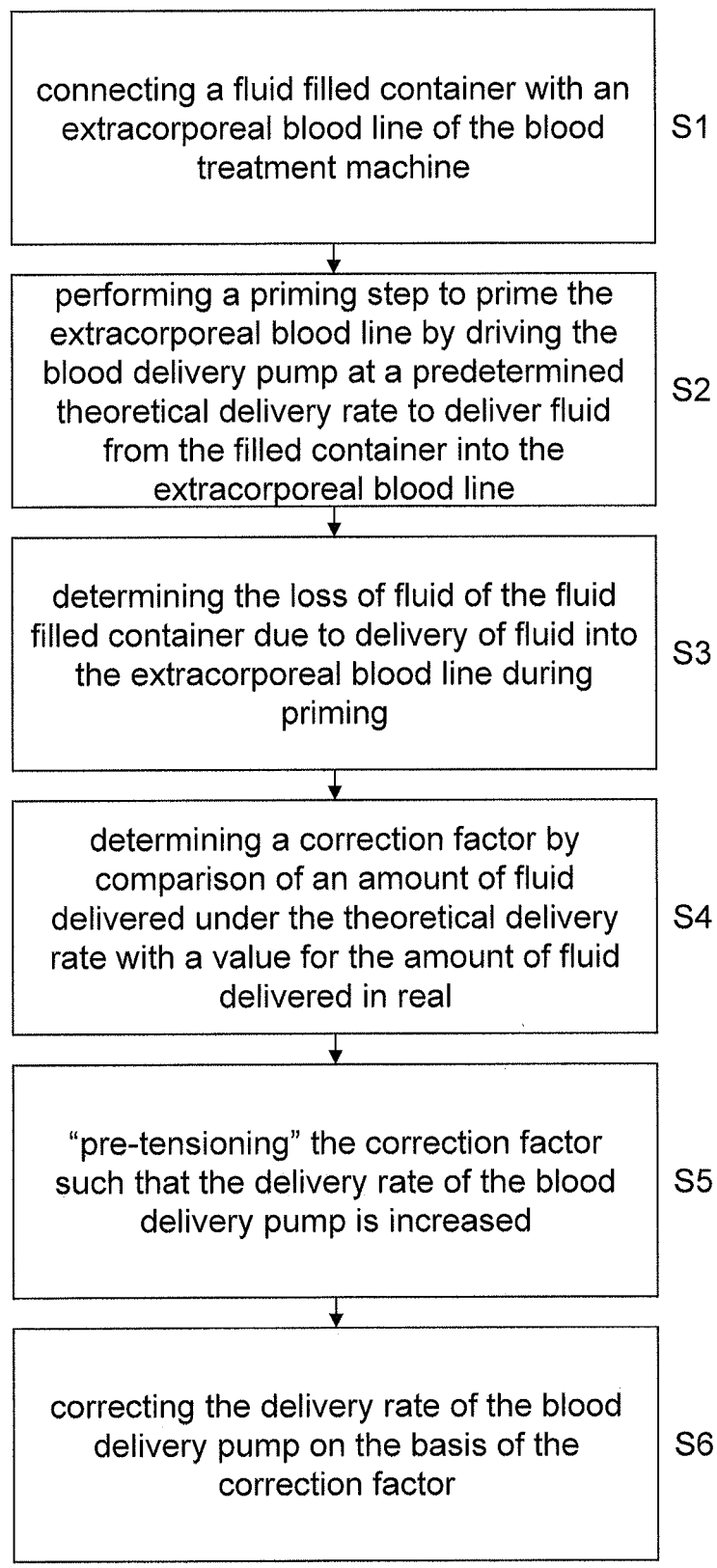
FIG. 2 shows a flow chart of a method for determining and adjusting a flow rate of a blood delivery pump of the blood treatment apparatus according to aspects of the invention.

FIG. 2 shows method steps for determining and adjusting the flow rate of the blood delivery pump 1 of the blood treatment apparatus according to aspects of the present invention. In step S1, the container 3, which is filled with fluid, is connected with the extracorporeal blood line of the blood treatment apparatus. In step S2, a priming step is performed so as to prime the extracorporeal blood line 5 by driving the blood delivery pump 1 at a predetermined theoretical delivery rate to deliver fluid from the container 3 into the extracorporeal blood line 5. In step 3, the loss of fluid of the fluid filled container due to delivery of fluid into the extracorporeal blood line 5 during priming is determined, e.g. by means of load cell 2. In step S4, a correction factor is determined by comparing a value for an amount of fluid delivered under the theoretical delivery rate with a value for an amount of fluid delivered in real. In step S5, the correction factor is "pre-tensioned" to a higher delivery rate, i.e. the correction factor is changed with a given extent such that the blood flow is kept within the acceptable tolerance range in the usual inlet "arterial" pressure range. In step S6, the delivery rate of the blood delivery pump 1 is adjusted on the basis of the correction factor.

By the present invention the calibration of the "pump segment constant" can be performed as part of an automatic priming process. This results in a quicker calibration and overall priming process. Additionally it ensures a very accurate calibration, since weight measurement happens before the disposable tubing set 5 and before the hemofilter 6 or dialyzer 6 and it is not influenced by air bubble removal during priming.

The invention claimed is:

1. A method for determining and adjusting a flow rate of a blood delivery pump of a blood treatment apparatus for renal replacement therapies, the method comprising:
   connecting a container filled with fluid with an extracorporeal blood line of the blood treatment apparatus for renal replacement therapies, the extracorporeal blood line including an arterial line, a venous line, and at least one of a hemofilter or a dialyzer arranged between the arterial line and the venous line;
   priming the extracorporeal blood line by driving the blood delivery pump at a predetermined delivery rate to deliver fluid from the container into the extracorporeal blood line;
   determining fluid loss of the container due to delivery of the fluid into the extracorporeal blood line during priming;
   determining a correction factor during priming by comparing an estimated value for an amount of fluid delivered based on the predetermined delivery rate with an actual value for an amount of fluid delivered at a determined actual delivery rate, the correction factor comprising a corrected drive signal required to operate the blood delivery pump at the determined actual delivery rate;
   modifying the correction factor to drive the blood delivery pump at a rate higher than the determined actual delivery rate; and
   operating the blood delivery pump using the modified correction factor during priming to keep deviation of flow delivered by the blood delivery pump within a predetermined acceptable tolerance range.

2. The method according to claim 1, further comprising the step of adjusting the flow rate of the blood delivery pump on the basis of the determined correction factor.

3. The method according to claim 1, wherein the fluid filled container is connected to the arterial line or an arterial port of the extracorporeal blood line.

4. The method according to claim 1, wherein the fluid loss during the priming is determined by measuring a weight of the container filled with fluid.

5. The method according to claim 4, wherein the weight of the container filled with fluid is measured by calculating the weight of the amount of fluid delivered into the extracorporeal blood line during the priming.

6. The method according to claim 1, wherein the blood delivery pump is a peristaltic pump.

7. The method according to claim 6, wherein the peristaltic pump has at least two pumping segments or pumping strokes.

8. The method according to claim 7, wherein an individual segment correction factor or stroke correction factor is determined for each pumping segment or stroke of the peristaltic pump.

9. The method according to claim 8, wherein the individual segment correction factor or stroke correction factor is increased to keep deviation of flow delivered by the blood pump within the predetermined acceptable tolerance range.

10. The method according to claim 1, wherein the container is a bag filled with saline.

11. The method according to claim 1, wherein a waste container is connected to an outlet of the extracorporeal blood line.

12. The method according to claim 11, wherein the waste container is connected to a venous line or a venous port of the extracorporeal blood line.

13. The method according to claim 1, wherein the predetermined delivery rate is constant during the priming.

14. The method according to claim 1, wherein the container is connected with an arterial inlet of the blood delivery pump.

15. The method according to claim 1, wherein the correction factor comprises a pump drive constant.

16. The method according to claim 15, wherein modifying the correction factor to drive the blood delivery pump at a rate higher than the determined actual delivery rate comprises reducing the value of the pump drive constant.

17. A blood treatment apparatus for renal replacement therapies, wherein said blood treatment apparatus comprises:
- an extracorporeal blood line including an arterial line, a venous line, and at least one of a hemofilter or a dialyzer arranged between the arterial line and the venous line;
- a container filled with fluid connected to the extracorporeal blood line;
- a blood delivery pump for delivering fluid from the container into an extracorporeal blood line; and
- determining means for determining fluid loss from the container due to delivery of fluid into the extracorporeal blood line; and
- a control apparatus that controls the blood delivery pump such that the fluid is delivered from the container into the extracorporeal blood line at a predetermined delivery rate, wherein:
  - the determining means determines the fluid loss from the container due to delivery of fluid into the extracorporeal blood line,
  - the control apparatus determines a correction factor by comparing of an estimated amount of fluid delivered under the predetermined delivery rate with the loss of fluid determined by the determining means to determine an actual delivery rate, the correction factor comprising a corrected drive signal required to operate the blood delivery pump at the actual delivery rate; and
  - the control apparatus modifies the correction factor to drive the blood delivery pump at a rate higher than the actual delivery rate, and operates the blood delivery pump using the modified correction factor to provide a higher delivery rate than the actual delivery rate to keep deviation of flow delivered by the blood pump within a predetermined acceptable tolerance range.

18. The blood treatment apparatus according to claim 17, wherein the control apparatus adjusts the flow rate of the blood delivery pump based on the correction factor.

* * * * *